United States Patent
Endara et al.

(10) Patent No.: US 10,478,224 B1
(45) Date of Patent: Nov. 19, 2019

(54) DISTRACTION CLAMP FOR TREATING INJURIES

(71) Applicants: Christopher D. Endara, Miami, FL (US); Matthew J. Endara, Palmetto Bay, FL (US)

(72) Inventors: Christopher D. Endara, Miami, FL (US); Matthew J. Endara, Palmetto Bay, FL (US)

(*) Notice: Subject to any disclaimer, the term of this patent is extended or adjusted under 35 U.S.C. 154(b) by 46 days.

(21) Appl. No.: 15/441,747

(22) Filed: Feb. 24, 2017

(51) Int. Cl.
    *A61B 17/00*     (2006.01)
    *A61B 17/64*     (2006.01)
    *A61B 17/66*     (2006.01)

(52) U.S. Cl.
CPC .......... *A61B 17/6466* (2013.01); *A61B 17/66* (2013.01)

(58) Field of Classification Search
CPC .............................................. A61B 17/60–666
See application file for complete search history.

(56) References Cited

U.S. PATENT DOCUMENTS

| | | | | |
|---|---|---|---|---|
| 4,541,422 A | * | 9/1985 | de Zbikowski | A61B 17/645 403/167 |
| 4,620,533 A | * | 11/1986 | Mears | A61B 17/645 606/54 |
| 5,356,411 A | * | 10/1994 | Spievack | A61B 17/7216 606/63 |
| 5,358,504 A | * | 10/1994 | Paley | A61B 17/66 606/105 |
| 6,022,348 A | * | 2/2000 | Spitzer | A61B 17/6466 606/324 |
| 6,409,729 B1 | * | 6/2002 | Martinelli | A61B 17/6466 606/59 |
| 6,565,564 B2 | * | 5/2003 | Hoffman | A61B 17/6466 606/59 |
| 7,041,103 B2 | | 5/2006 | Hoffmann-Clair et al. | |
| 7,048,735 B2 | | 5/2006 | Ferrante et al. | |
| 7,699,848 B2 | | 4/2010 | Hoffman et al. | |
| 7,722,609 B2 | | 5/2010 | Bordeaux | |
| 7,931,650 B2 | * | 4/2011 | Winquist | A61B 17/6458 606/59 |
| 8,361,120 B2 | | 1/2013 | Gabelberger et al. | |
| 8,403,928 B2 | | 3/2013 | Bordeaux | |
| 8,734,446 B2 | * | 5/2014 | Miller | A61B 17/6466 606/277 |
| 8,758,343 B2 | | 6/2014 | Maughan et al. | |
| 9,539,029 B1 | | 1/2017 | Muniz et al. | |

(Continued)

*Primary Examiner* — Nicholas J Plionis
*Assistant Examiner* — Steven J Cotroneo
(74) *Attorney, Agent, or Firm* — Malloy & Malloy, P.L.

(57) ABSTRACT

A distraction clamp for treating a variety of injuries, comprising a rod clamp assembly having two clamps each configured to retain a rod, a pin clamp assembly comprising a bracket having a first mating surface, and two retainers each having a second mating surface. The bracket is structured to retain a plurality of pins. The first and second mating surfaces of the bracket and retainers respectively, are disposed in movable, retaining engagement with one another. The bracket is reciprocally movable along its length relative to the rod clamp assembly and to the clamp connector. The clamp connector serves to interconnect the rod clamp assembly to the pin clamp assembly. The clamp connector may include a biasing structure disposed and configured to movably bias the bracket in a spaced relation relative to the rod clamp assembly.

9 Claims, 10 Drawing Sheets

(56) References Cited

U.S. PATENT DOCUMENTS

| | | | |
|---|---|---|---|
| 9,549,762 B2 * | 1/2017 | Thomke | A61B 17/6466 |
| 2009/0299368 A1 * | 12/2009 | Bauer | A61B 17/645 606/57 |
| 2010/0262143 A1 | 10/2010 | Bordeaux | |
| 2011/0066151 A1 | 3/2011 | Mürner et al. | |
| 2012/0004659 A1 * | 1/2012 | Miller | A61B 17/6466 606/54 |
| 2012/0089142 A1 * | 4/2012 | Mullaney | A61B 17/6466 606/54 |
| 2012/0209264 A1 * | 8/2012 | Zandona | A61B 17/6466 606/54 |
| 2013/0165931 A1 | 6/2013 | Bordeaux | |

* cited by examiner

DISTRACTION CLAMP FOR TREATING INJURIES

BACKGROUND OF THE INVENTION

Field of the Invention

The present invention relates to an external fixation device in the form of a distraction clamp for use in treatment of a variety of injuries including, but not limited to, injuries to the lower leg, ankle, and arm. More specifically, the present invention relates to a distraction clamp that will be applied to an affected area after an injury to stretch out the ligaments and damaged bone structure. The distraction clamp of the present invention operates so that the damaged bone structure can assume a position that will allow the affected area to heal and reduce inflammation either permanently or temporarily prior to surgical treatment or other medical treatment.

Description of the Related Art

A very common injury is fracture of the lower leg ether in the tibia or the fibula. Other common injuries include fractures to other parts of the body such arm bones. One existing method for treating these types of injuries include stabilization of the affected area via a cast or other immobilization structures. This method though is not always as effective compared to other existing methods of treating these types of injuries. One method uses a distraction clamp or an external fixator that will restore the damaged bone structure back into its normal position. This method involves attaching pins to the bone structure within the affected area. Typically, the pins are attached during a surgical procedure, and are removed after healing of the area or after further surgical intervention. Attaching pins to the bone structure is done in order to prompt the desired alignment that will best achieve healing of the affected area. As such, external fixators and distraction clamps work by attaching a plurality of pins to different parts of the bone structure. The different pins are connected to the devices and the affected area is stretched and positioned to achieve the desired alignment of the bone. Additionally, this process stretches the surrounding ligaments and corresponding muscle tissue therefore promoting healing and stability of the affected area. Existing devices include adjustable external fixators. Some of the existing devices include openings which may hold pins in an array of different positions. Other fixation devices incorporate clamps and rods which are movable and adjustable.

It would be beneficial to provide a distraction clamp incorporating some of the features of existing fixator devices, but also incorporating a movable pin retaining structure. It would be helpful if this pin retaining structure were reciprocally movable along its length, and selectively retainable in a variety of different positions, to provide optimal alignment and stretching of the injured area. Therefore, a benefit may be realized by providing a distraction clamp having a bracket that can retain a plurality of pins, and also having a corresponding set of retaining structures. It would be advantageous to provide a bracket and corresponding retaining structures both having mating surfaces so as to form a mating engagement that could facilitate movement and selective retention of the bracket in a variety of different positions. Another advantage could also be provided if the position of the bracket could be adjusted using only one hand. A further benefit may also be realized by providing a distraction clamp with a biasing structure to facilitate movement of the bracket.

SUMMARY OF THE INVENTION

The present invention is directed to a distraction clamp which generally comprises a structure configured to retain a plurality of pins attached to a bone, a structure configured to retain a plurality of rods, and a connector. More specifically, the distraction clamp of the present invention comprises a rod clamp assembly, a pin clamp assembly, and a clamp connector that interconnects the rod clamp assembly to the pin clamp assembly.

The pin clamp assembly generally comprises a bracket and a plurality of retainers. Preferably the pin clamp assembly should comprise two retainers. The bracket may come in the form of a solid piece, or may be formed by a plurality of interconnected pin clamp segments. The bracket, and in some embodiments the pin clamp segments, may be adjustable to receive and retain a plurality of pins attached to a bone. The bracket and the retainers will both have corresponding first and second mating surfaces to create a mating engagement between the bracket and the retainers. Both mating surfaces may come in the form of a plurality of spaced apart ribs configured in an adjustable threaded engagement. The mating engagement between the bracket and the retainers should generate a frictional resistance that permits selective retention of the bracket. However, the frictional resistance should not prevent reciprocal movement of the bracket in relation to the retainers. As such, movement of the bracket according to the present invention occurs in a direction substantially transverse to the length of the clamp connector and substantially along the length of the bracket. As such, the mating engagement between the bracket and the retainers permits movement and selective retention of the bracket relative to the retainers in a plurality of different positions.

The rod clamp assembly comprises a plurality of clamps configured to retain a rod. In preferred embodiments of the present invention, the rod assembly comprises two clamps. The clamps may comprise a plurality of clamp segments. Generally, each clamp comprises two clamp segments each disposed in spaced relation to one another. This spaced relation between the clamp segments forms a socket that retains a rod. The size of the socket may be adjusted to retain rods of varying dimensions. Preferred embodiments of the present invention may include sockets configured to retain rods of cylindrical shapes. But, clamps may also be configured to retain rods of varying shapes, not just cylindrical.

The rod clamp assembly of the present invention comprises a plurality of connectors. Each connector corresponds to each clamp of the rod clamp assembly. Each connector interconnects its corresponding clamp to the clamp connector. The connectors may comprise a plurality of openings. At least one opening will be structured to retain its corresponding clamp. The opening that retains the clamp may be in the form of an adjustable sleeve. In some preferred embodiments the size of the sleeve will be cylindrical. The size of the sleeve should be sufficient to retain a clamp in movable relation with respect to the connector. Thus, the clamp remains movable, and in some embodiments rotational, relative to its corresponding connector. Movement restriction members may be disposed on the clamp or the sleeve to facilitate selective retention of the clamp in a variety of orientations within the sleeve. Movement restriction devices may also be disposed on the clamp connector to also facilitate selective retention of the rod clamp assembly with respect to the pin clamp assembly.

The connector of the rod clamp assembly generally comprises a different opening configured to receive the clamp connector thereby interconnecting the rod clamp assembly to the rest of the distraction clamp. This opening of the connector should be of sufficient diameter so that the clamp connector may pass therethorugh. This opening may come in the form of a cylindrical channel to permit rotation of a clamp connector having a cylindrical shape. The connector is disposed in a movable, and in some embodiments a rotational, relation with respect to the clamp connector and with respect to the pin clamp assembly.

As previously mentioned the clamp connector of the present invention interconnects the rod clamp assembly to the pin clamp assembly. Preferred embodiments of the present invention include a clamp connector having an elongated cylindrical shape. An elongated cylindrical shape of the clamp connector is not always required as the distraction clamp of the present invention may comprise a clamp connector having other shapes. As mentioned above, the clamp connector interconnects connectors of the rod clamp assembly to the pin clamp assembly.

In some embodiments of the present invention, the connectors of the rod clamp assembly may also be disposed in mating engagement with respect to pin clamp assembly. More specifically, the connectors and the retainers may have corresponding second and third mating surfaces. These mating surfaces create a mating engagement that permits movement and selective retention of the connectors, and consequently the rod clamp assembly, relative to the retainers, and relative to the pin clamp assembly. Furthermore, the connectors may be disposed in a rotational relation to the clamp connector, to the retainers, and to the rod clamp assembly. The third and fourth mating surfaces of the connectors and the retainers may also comprise pluralities of spaced apart ribs cooperatively disposed to form a threaded engagement. In some embodiments, the spaced apart ribs may be disposed on the retainers and on the connectors in a radial pattern thereby enabling rotation and selective retention of the connectors relative to the retainers.

The clamp connector of the present invention may also comprise a biasing structure disposed and configured to movably bias the bracket in a spaced relation to the rod clamp assembly. The biasing structure may comprise springs or other mechanical devices. The biasing structure is configured to create a spaced relation between bracket and the rod clamp assembly. More specifically, the biasing structure forces a separation of the connectors with respect to the retainers. As such, there is not mating engagement between the connectors and the retainers disposing the pin clamp assembly, and more specifically the bracket, in a spaced relation to the rod clamp assembly. Generally, the bracket should remain reciprocally movable with respect to the rod clamp assembly regardless if the clamp connector comprises a biasing structure. However, the biasing structure facilitates this reciprocal movement of the bracket.

Additional features of the distraction clamp of the present invention comprise locking features. The present invention may comprise a locking member which disposes the distraction clamp in an "operative orientation." This "operative orientation" may be substantially defined as a movement restricting relation between the rod clamp assembly, the pin clamp assembly, and the clamp connector. In the "operative orientation", only the clamps should remain movable, and in some embodiments rotational, with respect to the connectors. In this "operative orientation" there should be no movement of the bracket with respect to the rod clamp assembly.

The locking member of the clamp connector may be formed by a driven engagement between the clamp connector and a nut. The clamp connector of the present invention may comprise a clamp connector having a threaded section. Additionally, the nut may have an opening with an internally threaded surface. The threaded section of the clamp connector may be disposed in driven engagement with the internally threaded surface of the nut. As such, the nut may be disposed in movable and driven engagement with respect to the clamp connector. The user may adjust, and in some embodiments rotate, the nut relative to the clamp connector. Relative rotation of the nut to the clamp connector will result in movement of the nut along the length of the threaded portion of the clamp connector.

Before the user adjusts the nut, the rod clamp assembly may be initially disposed in a movable and spaced relation relative to the pin clamp assembly. At this stage, the user has the ability to adjust the distraction clamp. After the user has finished adjusting the distraction clamp, the user may proceed to adjust the nut in order to dispose the distraction clamp in the "operative orientation". Adjustment of the nut will consequently force movement of the same along the length of the clamp connector. The nut will consequently induce at least one of the connectors to move along the length of the clamp connector. This relative movement of the connectors, and consequently the rod clamp assembly, will eliminate the spaced relation between the rod clamp assembly and the pin clamp assembly. Further adjustment of the nut will create a mating engagement between the retainers and the bracket, and between the connectors and the retainers. Even further adjustment of the nut will increase the frictional resistance between generated by this mating engagement thereby preventing any further movement of the bracket, retainers, and connectors.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying figures, one preferred embodiment of the distraction clamp of the present invention is generally indicated as 10 throughout. With primary reference to FIG. 1, the distraction clamp 10 includes a rod clamp assembly 20 interconnected by a clamp connector 40 to a pin clamp assembly 30. The rod clamp assembly 20 generally comprises two clamps generally indicated as 21. Each of the two clamps 21 is connected to the clamp connector 40, and each is dimensioned and configured to retain a rod. The clamps 21 may be made out of a plurality of clamp segments, and in at least one embodiment two clamp segments, generally indicated as 22 and 24. As shown in FIGS. 1-3 and 9-10, the clamp segments 22 and 24 may be disposed in a spaced relation so as to form a socket 25. By way of example only, the illustrative embodiments as shown in FIGS. 1-3 and 9-10 show a socket 25 formed by the two clamp segments 22 and 24 disposed in a spaced relation. As should become apparent, the size of the socket 25 may be adjusted to accommodate a variety of rods of different sizes. In the illustrative embodiments as shown in FIGS. 1-4 and 9-10, the size of the socket 25 may be adjusted by a clamp segment connector 23. The clamp segments 22 and 24 may comprise corresponding openings to receive the clamp segment connector 23.

Figure 4:
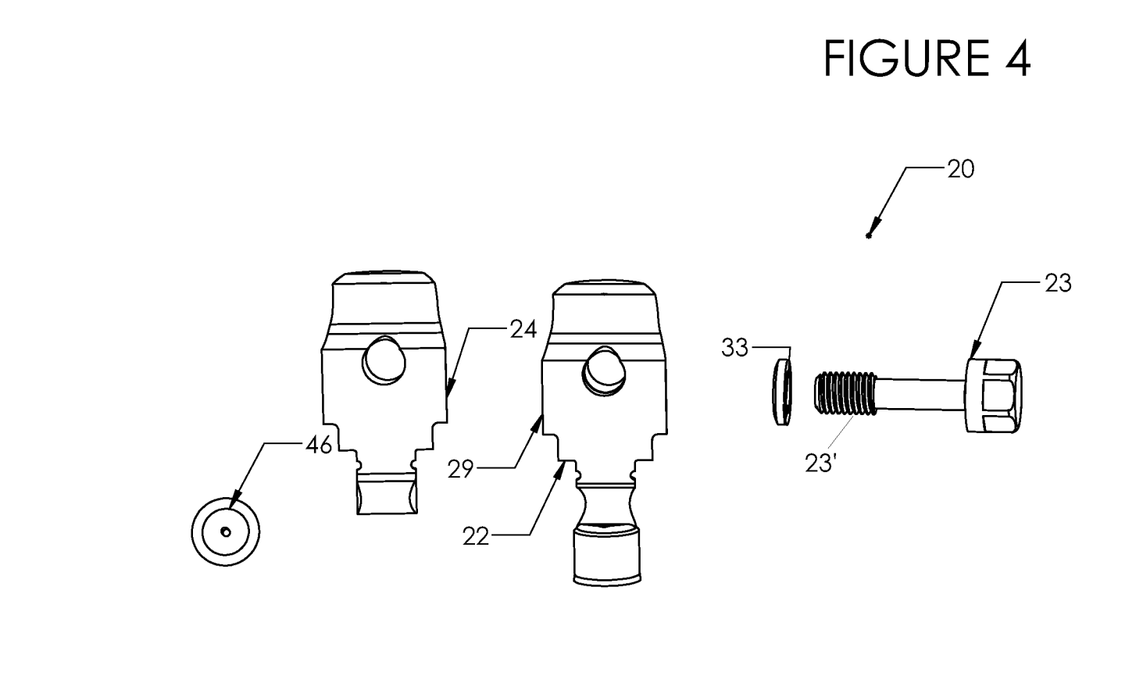
FIG. 4 is an exploded view of the embodiment as shown in FIG. 3.
Figure 5:
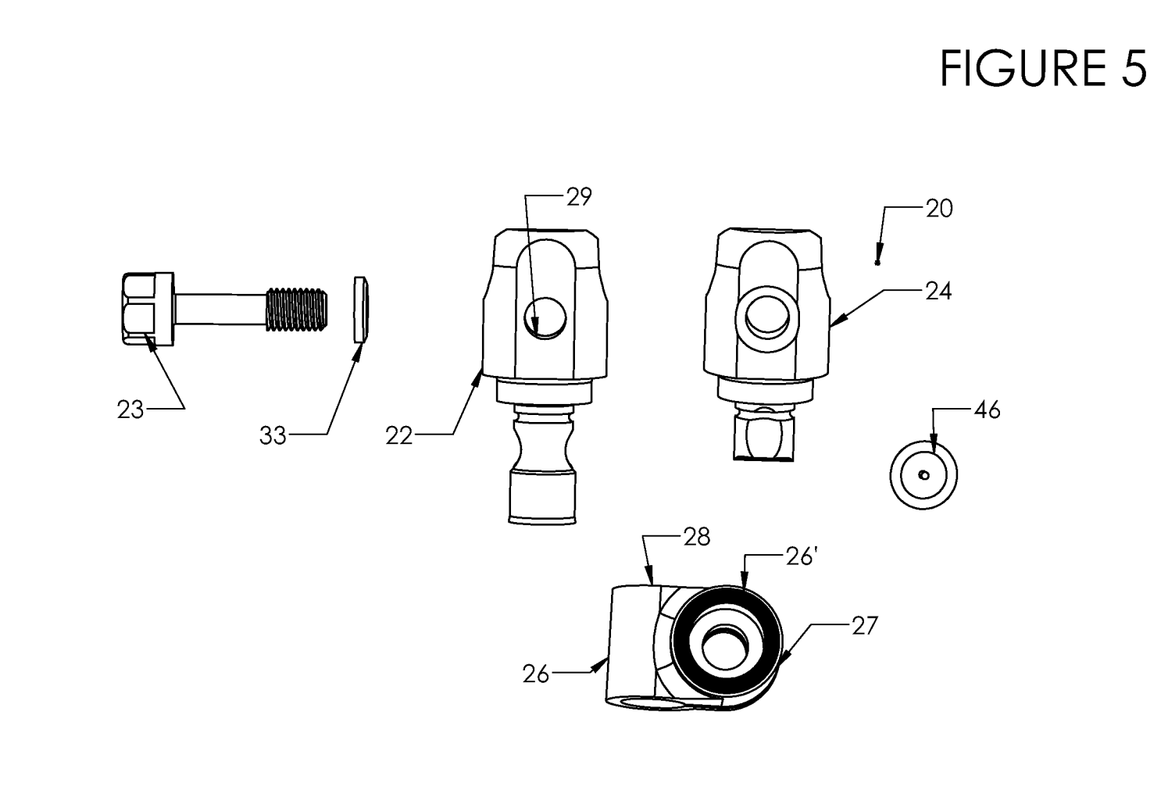
FIG. 5 is another exploded view of the embodiment as shown in FIGS. 3 and 4.

Furthermore, the clamp segment connector 23 may comprise a threaded portion 23'. The threaded portion 23' may be cooperatively disposed in driven engagement with respect to a corresponding structure, such as an internally threaded surface 29 of a clamp segment 22 or 24. This driven engagement serves to adjust the size of the socket 25. In the illustrative embodiment as shown in FIGS. 4-5, the clamp segment 22 comprises an internally threaded surface 29 that corresponds to the threaded portion 23' of the clamp segment connector 23. Accordingly, the threaded portion 23' of the clamp segment connector 23 may engage in driven relation with respect to the internally threaded surface 29 of the clamp segment 22 so that rotation of the clamp segment connector 23 in one direction will reduce the size of the socket 25. Conversely, rotation of the clamp segment connector 23 in an opposite direction will increase the size of the socket 25.

Figure 1:
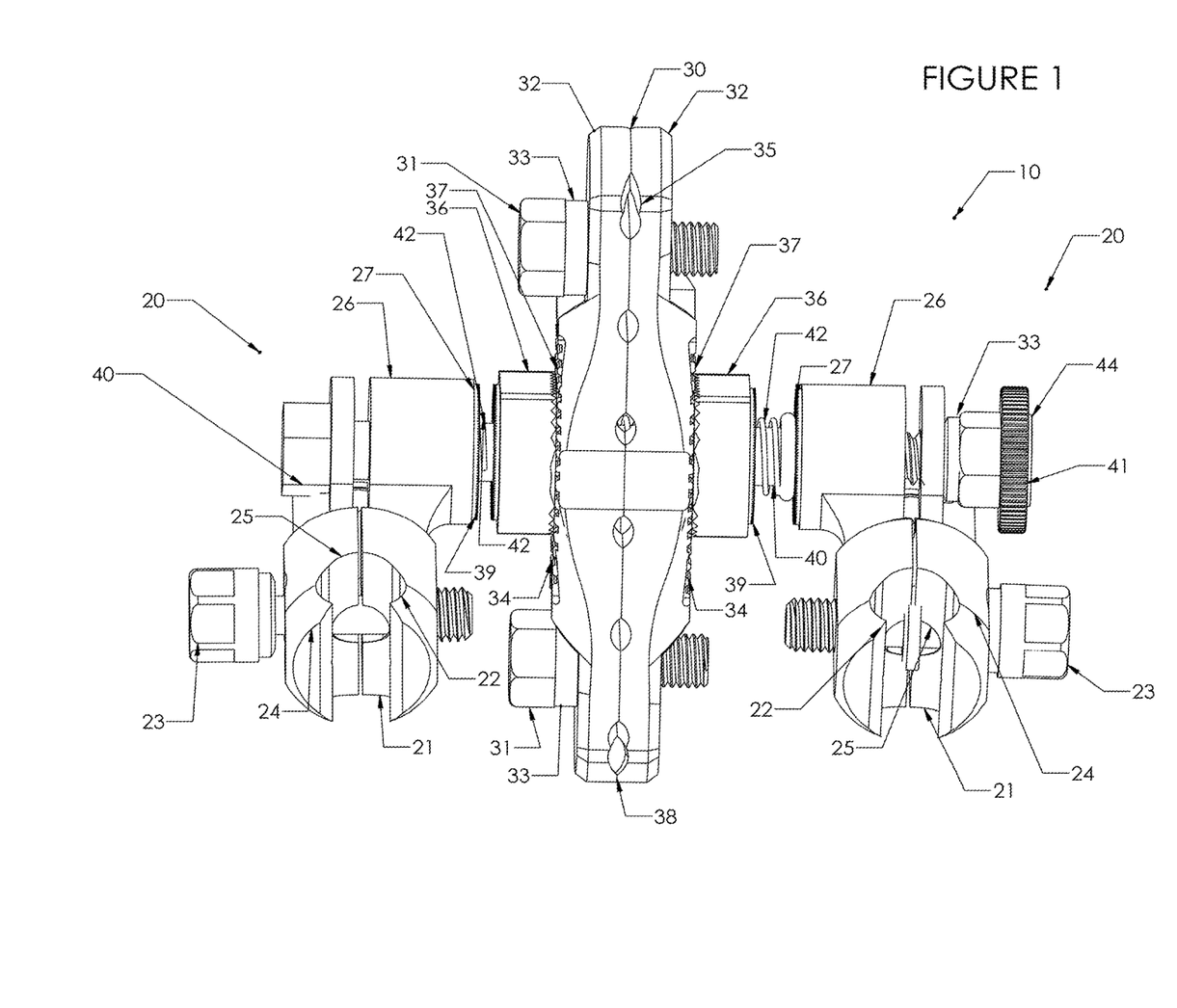
FIG. 1 is a top view of one preferred embodiment the distraction clamp of the present invention.
Figure 2:
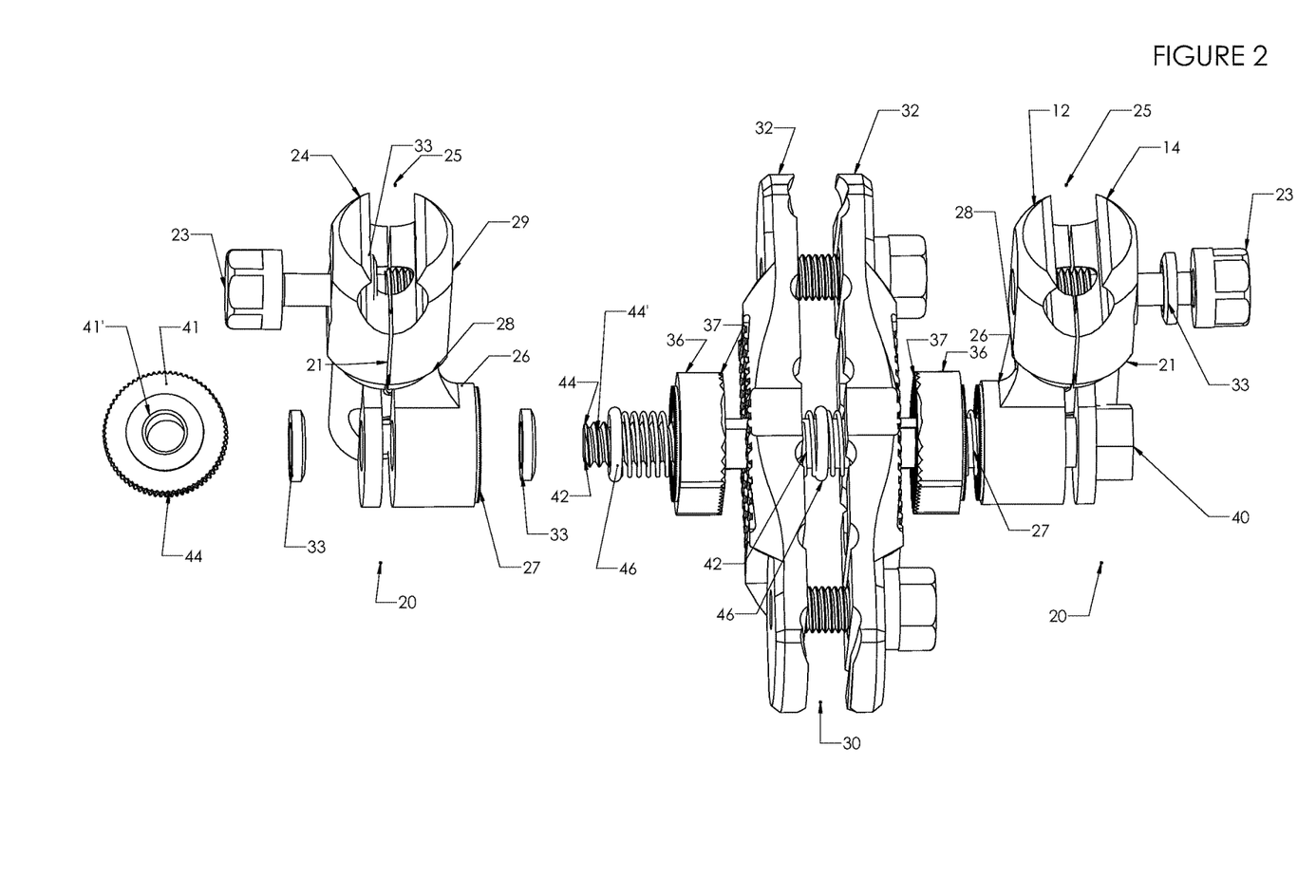
FIG. 2 is a perspective partially exploded view of one preferred embodiment of the distraction clamp of the present invention.
Figure 3:
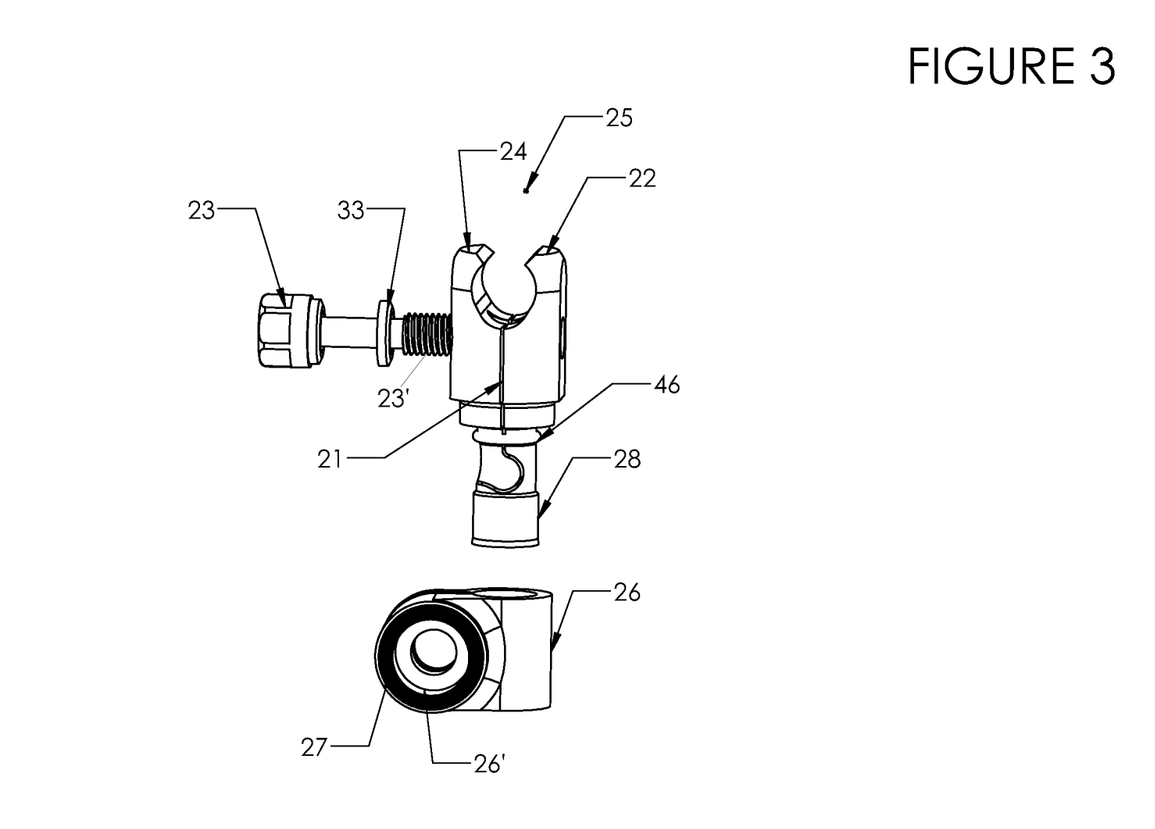
FIG. 3 is a side view of one preferred embodiment of part of the rod clamp assembly of the present invention.

As represented in FIGS. 1-3 and 9-10, the rod clamp assembly 20 of the distraction clamp 10 of the present invention may also comprise a plurality of connectors, generally indicated as 26. Each clamp 21 of the rod clamp assembly 20 should have one corresponding connector 26. The connector 26 serves to interconnect each clamp 21 to the clamp connector 40 and to the pin clamp assembly 30. The connector 26 may comprise a plurality of openings. In some embodiments the connector 26 may also comprise two openings. One opening interconnects the clamps 21 to the connector 26, and the other opening may be configured so that the clamp connector 40 may interconnect the rod clamp assembly 20 to the pin clamp assembly 30. The opening that interconnects the clamps 21 to the connector 26 may be in the form of a sleeve 28 or other retaining structure. The illustrative embodiment as shown in FIG. 3 comprises two openings; one opening being configured to receive the clamp connector 40, and the other being configured to receive and interconnect either of the clamps 21 to the connector 26.

Figure 9:
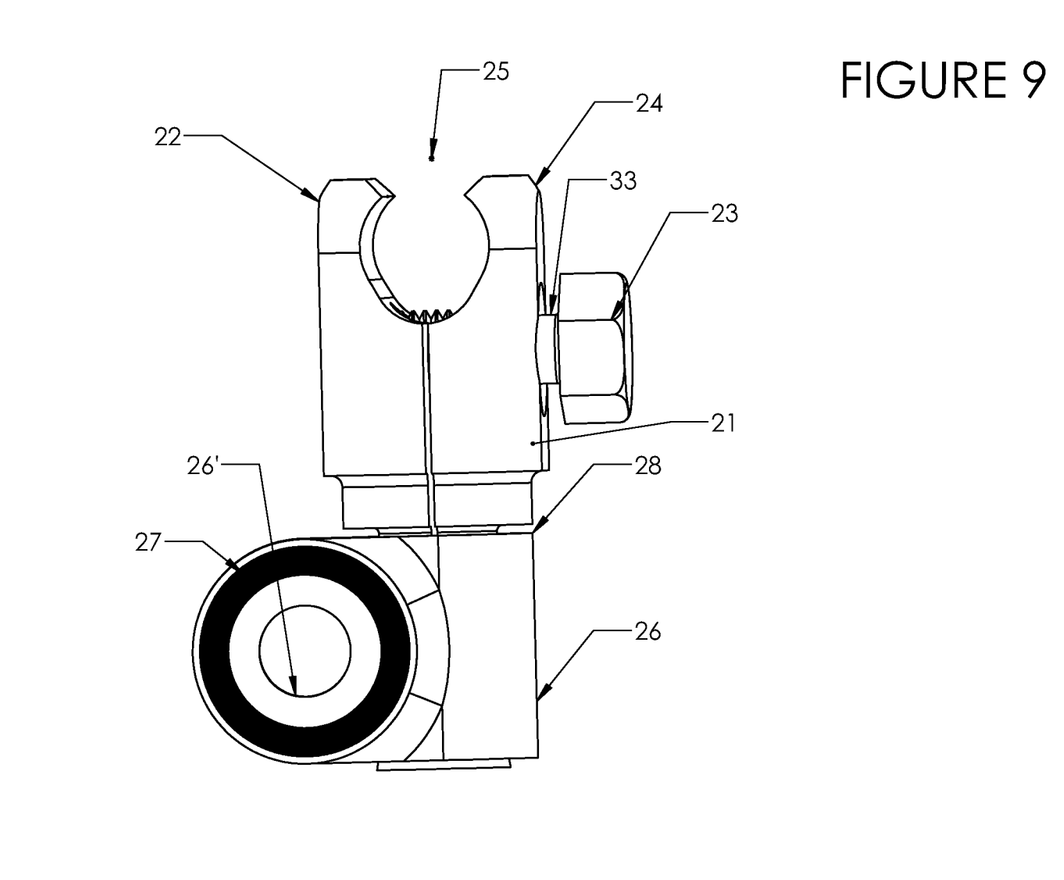
FIG. 9 is another side view of the embodiment as shown in FIG. 3.

The opening of the connector 26 configured to receive the clamp connector 40 may be in the form of a channel 26' having a cylindrical shape. In the illustrative embodiment as shown in FIGS. 3 and 9, a connector 26 comprises an opening having a channel 26'. Moreover, the clamp connector 40 may also have a cylindrical shape. As such, the clamp connector 40 may be configured to have a smaller diameter than the channel 26' of the connector 26 so that the clamp connector 40 may pass through the channel 26'. In some embodiments according to the present invention the cylindrical shapes of the clamp connector 40 and the channel 26' of the connector 26 result in the connector 26 being connected to and disposed in movable relation with respect to the clamp connector 40. In the illustrative embodiment as shown in FIG. 1, two different connectors 26 are interconnected to the clamp connector 40 and are cooperatively structured so that they can move, and in this illustrative embodiment rotate. In the illustrative embodiment as shown in FIG. 1, the two different connectors 26 may rotate, not only with respect to the clamp connector 40, but also with respect to the pin clamp assembly 30. It should be appreciated that the clamp connector 40 of the present invention may serve to movably interconnect, and in some embodiments rotationally interconnect, the rod clamp assembly 20 to the pin clamp assembly 30.

The distraction clamp 10 of the present invention is capable to disposing the rods in a rotational relation with respect to the connectors 26. Furthermore, the distraction clamp 10 of the present invention may also permit rotation of the connectors 26, and therefore rotation of the clamps 21 and rods, with respect to the an axis defined by the length of the clamp connector 40. This ultimately results in the rods being movable in several directions making the present invention advantageous in that the user will have great flexibility in adjusting the position of the rods.

The connector 26 according to the present invention may comprise a sleeve 28. As shown in the illustrative embodiment as represented in FIG. 3, the opening of the connector 26 configured to receive one of the clamps 21 may be in the form of a sleeve 28. Additionally, the sleeve 28 may be adjustable to accommodate the size of the clamp 21. As should become apparent, each connector 26 interconnects its corresponding clamp 21 to the clamp connector 40 thereby interconnecting the rod clamp assembly 20 to the pin clamp assembly 30. More specifically, and by way of example, the clamps 21 may be inserted inside the sleeve 28 of the connector 26, and the size of the sleeve 28 may be adjusted accordingly to ensure that the clamp 21 is retained within the sleeve 28. In some embodiments, the size of the sleeve 28 should be adjusted so that each clamp 21 is disposed in movable relation with respect its corresponding connector 26. In at least one embodiment of the present invention, the clamps 21 are not only movable, but also rotational with respect to their corresponding connector 26. Moreover, the clamps 21 may be rotational with respect to an axis defined by the length of the sleeve 28.

Each clamp 21 may comprise a movement restriction member, generally indicated as 46, which may be cooperatively disposed, dimensioned, and structured to facilitate selective rotation between each clamp 21 and its corresponding connector 26. The movement restriction member 46 may be configured in a variety of shapes, including but not limited to circular. Additionally, the movement restriction members 46 may be made out of a material such as, but not limited to, silicone, rubber, or another flexible material. Further, the movement restriction member 46 may be cooperatively configured with the corresponding connector 26, to result in a semi-restrictive rotation of the clamp 21, relative to the frame connector 26. As such, this semi-restrictive rotation may be defined by the movement of restriction member 46, which frictionally engages the interior of a corresponding surface. As an example, this interior of a corresponding surface may be the interior surface of the sleeve 28. As a result of this frictional engagement, the clamps 21 are maintained in place and cannot freely rotate unless the user supplies enough rotational force to overcome the frictional resistance between the movement restriction member 46 and corresponding surface. As will be explained in further detail later, additional movement restriction members 46 may also be used to achieve and maintain a selective retention of other components.

Figure 10:
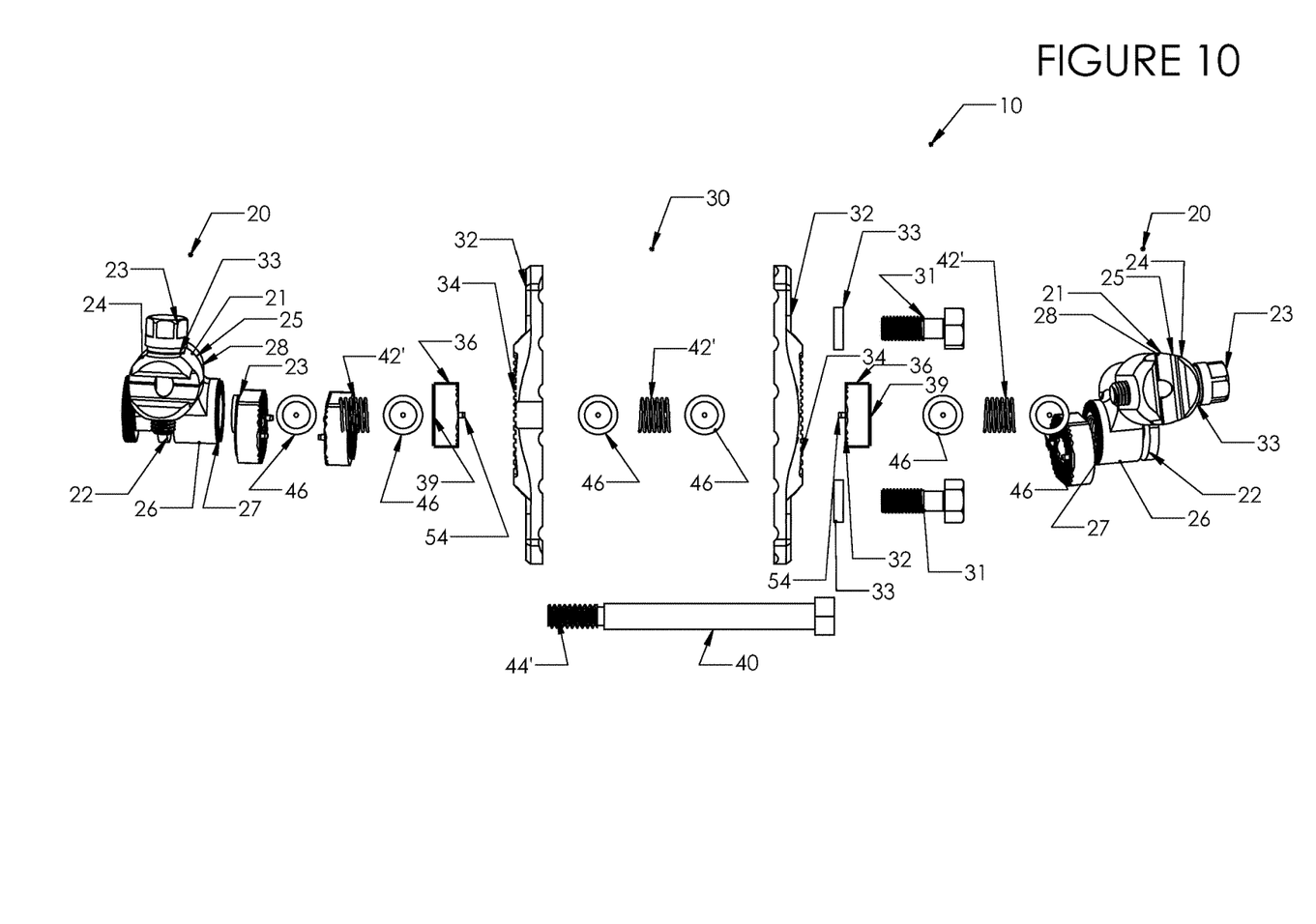
FIG. 10 is a top exploded view of the embodiment as shown in FIG. 1.

As will be explained in greater detail hereinafter, pin clamp assembly 30 of the distraction clamp 10 of the present invention includes a bracket 38 structured to retain a plurality of pins that will be attached to a bone. The bracket 38 may be a solid piece or may be formed by a plurality of interconnected pin clamp segments 32. In some embodiments, the bracket 38 is formed by interconnecting two pin clamp segments 32. The illustrative embodiment as shown in FIGS. 1-2 and 10 shows two pin clamp segments 32 interconnected to one another and thus forming a bracket 38. Generally, the bracket 38 comprises a plurality of pin openings 35 which may configured to retain corresponding pins. The size of the openings 35 may be adjusted to match size of the corresponding pin. With reference to the illustrative embodiment as shown in FIG. 1, a bracket 38 is formed by two pin clamp segments 32 being interconnected by two different bracket connectors 31. If needed, more than two bracket connectors 31 may be used.

As with the clamp segment connector 23, the bracket connector 31 may also have a threaded surface. Furthermore a washer, generally indicated as 33, may be used to better adjust and secure bracket connector 31 to the pin clamp segments. Other washers 33 may also be used accordingly to facilitate connections between different parts of the distraction clamp 10. Additionally, and similar to the internally threaded surface 29 of the clamp segment 22, either of the two pin clamp segments 32 may also comprise openings with internally threaded surfaces. As such the bracket connectors 31 may be similarly disposed in driven engagement with the interior threaded surface of the pin clamp segments 32. Thus, the bracket connector 31 not only serves to interconnect the pin clamp segments 32, but also serves to adjust the size of the pin openings 35. As should become apparent, rotation in one direction of the bracket connector 31 will increase the size of the pin openings 35 while rotation in the opposite direction will decrease the size of the pin openings 35.

Figure 7:
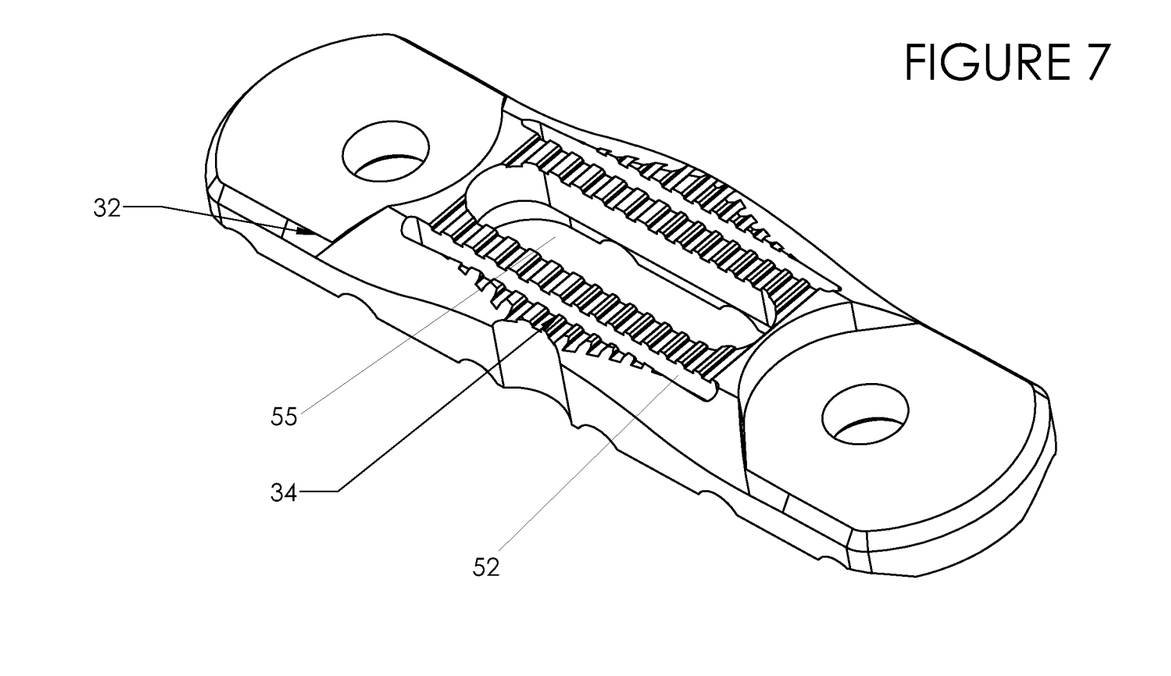
FIG. 7 is a side view of one embodiment of a pin clamp segment according to the distraction clamp of the present invention.

Preferred embodiments of the pin clamp assembly 30 of the distraction clamp 10 according to the present invention generally comprise a plurality of retainers, generally indicated as 36. In at least one embodiment, the rod clamp assembly 20 should have two retainers 36. Moreover, the bracket 38 generally comprises a first mating surface, indicated as 34. Likewise, each of the retainers 36 comprise a corresponding second mating surface, indicated as 37. The first mating surface 34 of the bracket 38 may be formed on each of the individual pin clamp segments 32. By way of example, the illustrative embodiment as shown in FIG. 7 shows a first mating surface 34 formed on one side of a pin clamp segment 32. As such, each of the two pin clamp segments 32 may have a first mating surface 34. This results in the bracket 38 having a first mating surface 34 on either side. Alternatively, if the bracket 38 is made of a solid piece, a first mating surface 34 may be formed on one or more sides of the bracket 38. The illustrative embodiment as shown in FIG. 1 shows a bracket 38 having a first mating surface 34 formed on either side.

Figure 6:
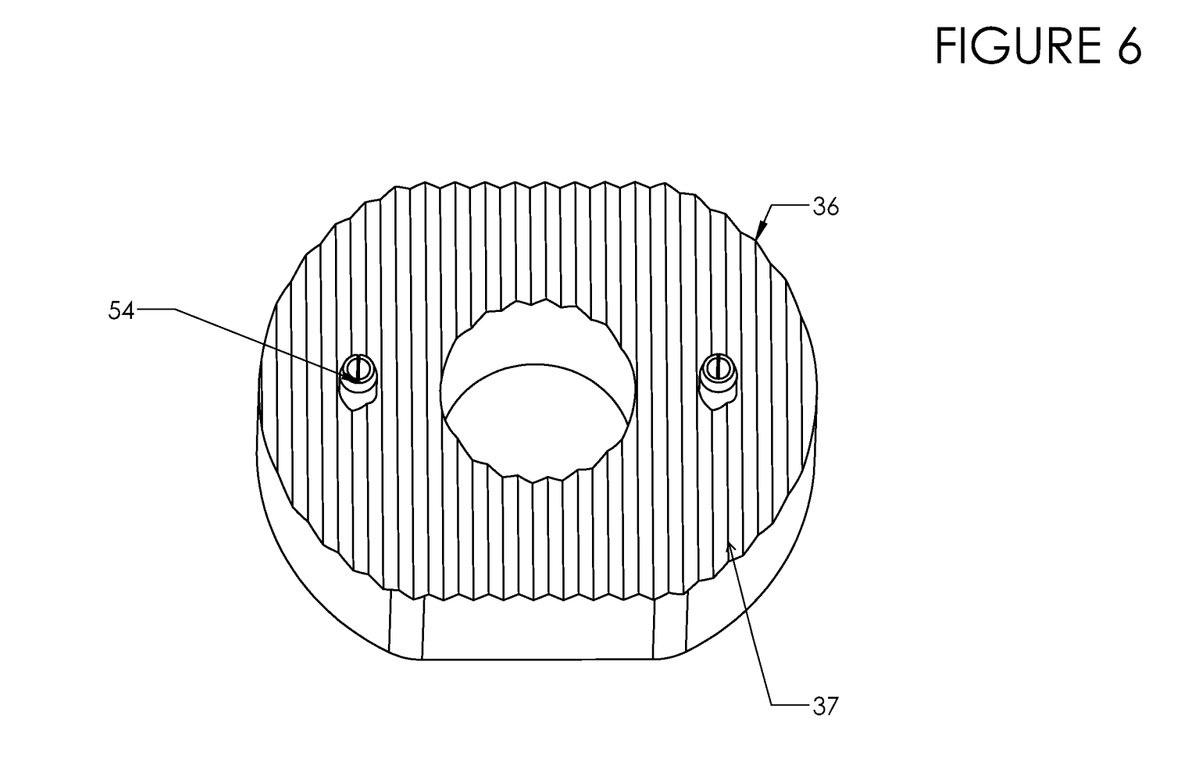
FIG. 6 is a top view of one preferred embodiment of part of the pin clamp assembly of the present invention.

Generally, the first mating surface 34 of the bracket 38 and the corresponding second mating surface 37 of the retainers 36 will be disposed in movable and retaining engagement with one another. In order to achieve this movable and retaining engagement, either or both of the first mating surface 34 and second mating surface 37 may comprise a plurality of spaced apart ribs cooperatively structured to define a threaded engagement. The illustrative embodiment as shown in FIG. 6 shows a retainer 36 having a second mating surface 37 that has a plurality of spaced apart ribs. Similarly, the illustrative embodiment as shown in FIG. 7 shows a pin clamp segment 32 having a first mating surface 34 also having a plurality of spaced apart ribs. Generally, a retaining engagement, may be achieved when both the first and second mating surfaces 34 and 37 of bracket 38 and retainer 36 are disposed in mating engagement with one another. Moreover, an adjustably threaded engagement may be achieved when both sets of spaced apart ribs of the first and second mating surfaces 34 and 37 are disposed in a cooperative mating engagement that permits selective movement of the bracket 38 with respect to the retainers 36. By way of example only, a retaining engagement of corresponding first and second mating surfaces 34 and 37 is shown in the embodiment as represented in FIG. 1. The cooperative engagement between the first and second mating surfaces 34 and 37 should provide enough frictional resistance so that the bracket 38 will be retained in place, unless the user supplies sufficient force to move the bracket 38 with respect to the clamp connector 40 and the rod clamp assembly 20. Therefore, the frictional resistance and/or "threaded engagement" created by the engagement between the first and second mating surfaces 34 and 37 should not prevent movement of the bracket 38 with respect to the retainers 36, the clamp connector 40 and the rod clamp assembly 20. As will be explained in further detail—hereinafter, the clamp connector 40 may comprise a locking structure 44 which may be used to control the frictional resistance of the mating engagement between the first and second mating surfaces 34 and 37.

The locking structure 44 may comprise a threaded section 44' disposed on one end of the clamp connector 40. In at least one embodiment according to the present invention, the locking structure 44 may have a nut 41. The nut 41 may have a cylindrical opening with an internally threaded surface 41'. The threaded section 44' of the locking structure 44 may be configured to achieve a mating and driven engagement with the internally threaded surface 41' of the nut 41. After such a mating and driven engagement is achieved between the threaded section 44' of the locking structure 44 and the internally threaded surface 41' of the nut 41, the clamp connector 40 should remain movable, and more specifically rotational, with respect to the nut 41.

The locking structure 44 of the clamp connector 40 may be configured to dispose both the rod clamp assembly 20 and the pin clamp assembly 30 in a movement restricting relation. This movement restricting relation therefore disposes the distraction clamp 10 in an "operative orientation". This "operative orientation" may be defined as a cooperative mating engagement between the rod clamp assembly 20, the pin clamp assembly 30, and the clamp connector 40. This cooperative mating engagement prevents movement, and more specifically, rotation of the connectors 26 of the rod clamp assembly 20 relative to the pin clamp assembly 30. Furthermore, this cooperative mating engagement also prevents movement of the bracket 38 with respect to the retainers 36, and also prevents movement of the bracket 38 with respect to the rod clamp assembly 20. Thus, in the "operative orientation" of the distraction clamp 10, only the clamps 21 may remain movable, and in some embodiments rotational, with respect to their corresponding connectors 36 and with respect to the pin clamp assembly 30.

As stated previously, the clamp connector 40 may be configured in a cylindrical shape, and may also be configured in different sizes. With reference to the illustrative embodiment as represented in FIG. 9, the connector 26 of the present invention may also comprise an opening in the form of a channel 26' having a cylindrical shape. The channel 26' may have a sufficiently larger size than that of the clamp connector 40. In some embodiments according to the present invention, both the channel 26' and the clamp connector 40 have cylindrical shapes wherein the diameter of the channel 26' is greater than the diameter of the clamp connector 40. As such, the clamp connector 40 may pass through the channel 26' therefore permitting relative rotation of the rod clamp assembly 20 relative to the clamp connector 40 and the pin clamp assembly 30.

Figure 8:
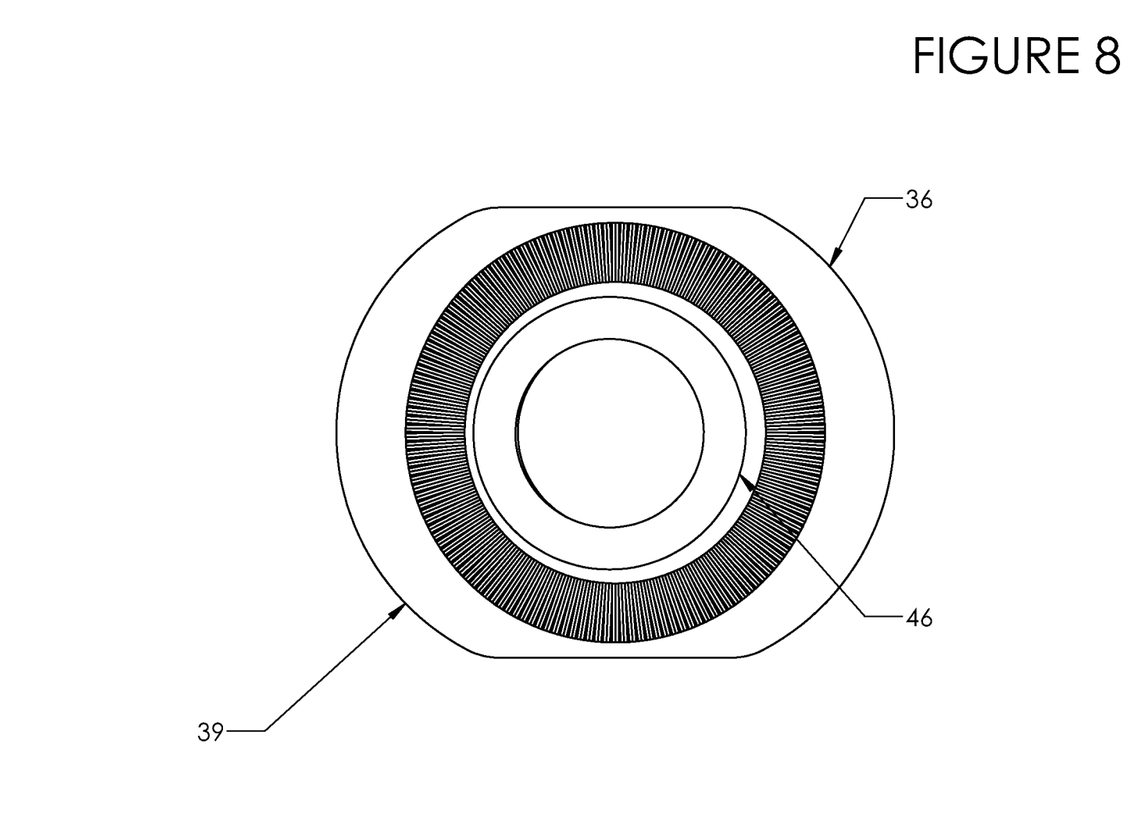
FIG. 8 is a top view of one embodiment of a retainer of a pin clamp assembly according to the distraction clamp of the present invention.

Additional features of the clamp connector 40 are represented in FIGS. 2 and 10. As previously mentioned, other parts of the distraction clamp 10 according to the present invention may comprise additional movement restriction members 46. For example, the clamp connector 40 may comprise a plurality of movement restriction members 46 that help to dispose and retain the rod clamp assembly 20 in a plurality of different positions or orientations relative to the pin clamp assembly 30. As previously mentioned, the movement restriction members 46 may have a circular shape, and may be made out of a variety of materials that create a semi-restrictive rotation. The frictional resistance of the movement restriction members 46 should be sufficient to maintain a desired position or orientation of the rod clamp assembly 20. But, at the same time, the frictional resistance should allow the user to supply enough rotational force to adjust the position of the rod clamp assembly 20. As previously described in greater detail, the movement restriction members create a frictional resistance when disposed against a corresponding surface. In this case, corresponding surfaces may include the interior surfaces of either opening of the connectors 26. The illustrative embodiment as shown in FIG. 8 shows a movement restriction member 46 disposed on an opening of the connector 26. Other corresponding surfaces may include surfaces within an inside of the bracket 38, or in at least one embodiment, surfaces inside either or both of the pin clamp segments 32 which form the bracket 38. As can be appreciated, once the movement restriction members 46 are disposed within the clamp connector 40, and rod clamp assembly 20 and the pin clamp assembly 30 are interconnected by the clamp connector 40, the movement restriction members 46 within the clamp connector 40 will provide sufficient frictional resistance to retain the rod clamp assembly 20 after the user adjusts its position. The movement restriction members 46 therefore can prevent free movement and rotation of the rod clamp assembly 20 with respect to the pin clamp assembly 30. The rod clamp assembly 20 has two clamps 21 each being independently movable, and more specifically independently rotational, relative to the clamp connector 40, and relative to the pin clamp assembly 30. For example, one of the two clamps 21 may be moved and rotated while the other clamp 21 may remain stationary. As such, one clamp 21 may move or rotate without the other clamp 21 having a corresponding movement or rotation.

The clamp connector 40 of the distraction clamp 10 of the present invention may also comprise a biasing structure 42. This biasing structure may be disposed on the clamp connector 40. Additionally, the clamp connector 40 may be manufactured with an internal biasing structure. In one embodiment according to the present invention, the biasing structure 42 may comprise a plurality of springs 42', and in some embodiments three springs 42', disposed on the clamp connector 40. With reference to the illustrative embodiment as shown in FIG. 10, one spring 42' may be disposed between each connector 26 and each retainer 36. Another spring 42' may be disposed inside of the bracket 38. The biasing structure 42, and more specifically the springs 42' may be made out of a variety of materials including, but not limited to steel, stainless steel, or different metal alloys. Several other combinations between the location and number of movement restriction members may also exist according to the preference of the user.

The biasing structure 42 forces a separation between the rod clamp assembly 20 and the pin clamp assembly 30. For example, the biasing structure 42 should be elastic enough to permit a retaining engagement between the rod clamp assembly 20 and the pin clamp assembly 30. The biasing structure should also permit movement of the rod clamp assembly 20 with respect to the pin clamp assembly 30. Additionally, the biasing structure 42 should also permit a spaced relation of the bracket 38 relative to the retainers 36. This spaced relation between the bracket 38 and the retainers 36 consequently permits linear and reciprocal movement of the bracket 38 relative to the pin clamp assembly 30 and to the rod clamp assembly 20. In a preferred embodiment according to the present invention, this linear and reciprocal movement is substantially parallel to an axis defined by the length of the bracket 38, and substantially transverse relative to the rod clamp assembly 20. Once the pins are retained within the bracket 38 and attached to the bone, the ability of the bracket to reciprocally move will allow the user to adjust the position of the distraction clamp 10 relative to the bone. The biasing structure 42 is a feature that facilitates reciprocal movement of the bracket 38 relative to the rod clamp assembly 20. But, a biasing structure 42 is not always required in order to enable reciprocal movement of the bracket 38 with respect to the rod clamp assembly 20. Some embodiments of the present invention are operational without the use of a biasing structure 42. A retaining engagement according to the present invention, between the first and second mating surfaces 34 and 37 of the bracket 38 and retainer 36 respectively, is what permits reciprocal movement of the bracket 38 with respect to the rod clamp assembly 20.

Another feature of the distraction clamp 10 of the present invention is that the user may adjust the locking structure 44 of the clamp connector 40 to dispose the rod clamp assembly 20 and the pin clamp assembly 30, in either a mating engagement or in a spaced relation. The illustrative embodiments as showing in FIGS. 1 and 10 show a clamp connector 40 having a locking structure 44. The locking structure 44, as shown in the illustrative embodiments of FIGS. 1 and 10, comprise a locking structure 44 with a threaded section 44' cooperatively be configured to achieve a mating and driven engagement with an internally threaded surface 41' of a nut 41. Due to the driven engagement between the nut 41 and the threaded section 44', rotation in one direction of the nut 41 will result in a substantially parallel movement of the nut 41 with respect to the clamp connector 40. This movement of the nut 41 will further induce movement of the rod clamp assembly 20 in a way that eliminates any spaced relation between the rod clamp assembly 20 and the pin clamp assembly 30. As such, the induced movement of the rod clamp assembly 20 will occur in a direction substantially parallel to the length of the clamp connector 40. More specifically, each connector 26 will move along an axis defined by the length of the clamp connector 40, and towards its corresponding retainer 36 so that a spaced relation no longer exists between the connector 26 and its corresponding retainer 36. In at least one embodiment according to the present invention, further rotation of the nut 41 in the same direction will create a retaining engagement between first and second mating surfaces 34 and 37 of the bracket 38 and the retainer 36 respectively.

Conversely, rotation of the nut 41 in an opposite direction will result in a spaced relation between the rod clamp assembly 20 and the pin clamp assembly 30. More specifically, rotation of the nut 41 will result in a spaced apart relation between the connector 26 and its corresponding retainer 36, and between the retainer 36 and the bracket 38. This spaced apart relation releases the retaining engagement achieved by the first and second mating surfaces 34 and 37 of the bracket 38 and the retainer 36 respectively, thereby disposing the bracket 38 in a movable relation with respect to the retainers 36 and the rod clamp assembly 20. The user may rotate the nut 41 accordingly to achieve a retaining engagement that will selectively maintain the bracket 38 in place, but at the same time will permit movement of the bracket 38 when the user supplies enough force.

The bracket 38, and in some embodiments the pin clamp segments 32 that form the bracket 38, may have an opening of sufficient size so that the clamp connector 40 can pass therethorugh. Additionally, the retainers 36 may also comprise openings of sufficient size so that the clamp connector 40 can also pass through the retainers 36. The retainers 36 as represented in FIGS. 6 and 8 comprise openings of a size larger than the diameter of a clamp connector 40, as shown for example in FIG. 10. With this configuration, the rod clamp assembly 20 may only rotate with respect to the length of the clamp connector 40 and with respect to the opening of the retainers 36. Thus, the clamp connector 40, the rod clamp assembly 20, and the pin clamp assembly 30 remain stationary with respect to the length of the bracket 38. At the user's option, the bracket 38 may be moved to dispose the distraction clamp 10 in a desired position relative to the bone. In at least one embodiment according to the present invention, a range of linear and reciprocal movement of the bracket 38 may be defined by the span of the opening of either the bracket 38, or in other embodiments the span of the opening of the pin clamp segments 32 that form the bracket 38. The illustrative embodiment as show in FIG. 7 shows a pin clamp segment 32 with an opening configured to permit movement of the pin clamp segment 32, and consequently the bracket 38, according to the span of the opening.

Additional structural features of the distraction clamp 10 of the present invention include selective movement and retention of the rod clamp assembly 20 with respect to the pin clamp assembly 30. In at least one embodiment according to the present invention, the connectors 26 may comprise a third mating surface, indicated as 27. Likewise, the retainers 36 may comprise a corresponding fourth mating surface, indicated as 39. Similar to the mating engagement between the first mating surface 34 of the bracket 38 and the second mating surface 37 of the retainer 36, the third mating surface 27 of the connectors 26 and the fourth mating surface 39 of the retainers 36 are also disposed in adjustable retaining engagement with respect to one another defining a "variable orientation" of the rod clamp assembly 20. Thus, relative rotation of the rod clamp assembly 20 may occur about an axis substantially defined by the length of the clamp connector 40. As such, relative rotation may occur between the rod clamp assembly 20 between the pin clamp assembly 30. Additionally, the retaining engagement between the third and fourth mating surfaces 27 and 39 will maintain the rod clamp assembly 20 in the desired orientation.

Subsequently, the user may further rotate the rod clamp assembly 20 in the same or a different direction and the retaining engagement of the third and fourth mating surfaces 27 and 39 will likewise maintain the desired orientation of the rod clamp assembly 20. In at least one embodiment of the present invention, the third and fourth mating surfaces 27 and 39 may also comprise a plurality of spaced apart ribs cooperatively structured to collectively define an adjustable threaded engagement with one another. The spaced apart ribs of the third and fourth mating surfaces 27 and 39 may be configured in a radially threaded configuration. The illustrative embodiments as shown in FIG. 8 shows a retainer 36 having a fourth mating surface 39 having spaced apart ribs disposed in a radial direction thus forming a different threaded configuration than previously explained.

Yet additional features of the distraction clamp 10 according to the present invention include stability of the bracket 38 to ensure substantially transverse movement of the same with respect to the rod clamp assembly 20. In at least one embodiment according to the present invention, stability of the movement of the bracket 38 is achieved via a plurality of elongate grooves 52 formed on the bracket 38, and via a plurality of pins 54 formed on the retainers 36. Some embodiments according to the present invention may comprise a plurality of grooves 52 formed in either or both of the pin clamp segments 32 that form a bracket 38. Reference may be had to the illustrative embodiment as shown in FIG. 7 which shows a plurality of grooves 52, and in this case two grooves 52, formed on a pin clamp segment 32. The illustrative embodiment as shown in FIG. 6 shows a plurality of pins 54, and specifically two pins 54, formed on a retainer 36. In at least one embodiment, the plurality of grooves 52 should be formed on the surface of the bracket 38 that will be disposed in retaining engagement with the retainer 36, namely the first mating surface 34. Similarly, the plurality of pins 54 should be formed on the surface of the retainer 36 which will be disposed in mating engagement with the bracket 38, the second mating surface 37. Each of said plurality of pins 54 corresponds to one of said plurality of grooves 52, and both are cooperatively oriented and movably interconnected to one another. This cooperative orientation between the corresponding ones of said plurality of pins 54 and said plurality of grooves 52 will ensure that the bracket 38 can maintain a reciprocal, substantially transverse movement of the bracket 38 to the clamp connector 40, the rod clamp assembly 20 and the retainers 36. More specifically, the grooves 52 should be of sufficient size and span to receive their corresponding pins 54, and to permit linear movement of the pins 54 along the length of the grooves 52. In cooperation therewith, the clamp connector 40 passes through an elongated slot 55 formed in and extending along the length of each of the pin clamp segments 32 of the bracket 38, thereby facilitating the aforementioned reciprocal movement of the bracket 38, along its length, in a direction transverse to the clamp segment 40. In preferred embodiments according to the present invention, there should be a minimum of two sets of corresponding grooves 52 and pins 54 formed on the bracket 38 and retainer 36 respectively. A minimum of two sets of grooves 52 and pins 54 will provide at least two different points of stability therefore preventing any pivotal movement or rotation of the retainers 36 with respect to the bracket 38. As an illustration, the plurality of pins 54 as shown in the embodiment as shown in FIG. 6 may be interconnected to the plurality of grooves 52 of the embodiment as shown in FIG. 7.

It should be noted that once the user has adjusted the distraction clamp 10, the user can the dispose the same in the "operative orientation". In at least one embodiment according to the present invention, two distraction clamps 10 each having two clamps 21, should be used. Each rod should be attached on one end by a clamp 21 of a distraction clamp 10, and on another end by a different clamp 21 of a different distraction clamp 10. One advantage of the distraction clamp 10, and more specifically the pin clamp assembly 30 of the present invention, is that the user does not need to use both hands, and can simply use one hand to adjust the position of the distraction clamp 10 relative to the bone. This is advantageous when the user may need to hold or operate other pieces equipment with the other hand. For example, the user may use one hand to adjust the position of the bracket 38, and use another hand to operate the locking structure 44.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A distraction clamp for treating injuries, comprising:
   a rod clamp assembly having two clamps each configured to retain a rod,
   a pin clamp assembly comprising a bracket having a first mating surface, and two retainers each having a second mating surface, said bracket structured to retain a plurality of pins,
   a clamp connector interconnecting said rod clamp assembly to said pin clamp assembly,
   said first and second mating surfaces of correspondingly disposed ones of said bracket and said two retainers disposed in movable, retaining engagement with one another,
   said first and second mating surfaces each including a plurality of spaced apart parallel ribs cooperatively structured to collectively define an adjustable threaded engagement with one another,
   a plurality of grooves and a plurality of pins respectively formed on said bracket and said retainers independently of said plurality of spaced apart parallel ribs, said plurality of grooves and said plurality of pins movably interconnected and cooperatively oriented to maintain a transverse movement of said bracket relative to said clamp connector and said rod clamp assembly, and
   said bracket reciprocally movable along its length on and in transverse relation to said clamp connector and said rod clamp assembly.

2. The distraction clamp as recited in claim 1 wherein each of said two clamps comprises two clamp segments disposed in spaced relation to one another, each of said two clamp segments disposed and configured to define a socket there between, said socket structured to retain a rod.

3. The distraction clamp as recited in claim 2 wherein each of said two clamps include a clamp segment connector adjustably interconnecting corresponding ones of said two clamp segments, each clamp segment connector disposed and structured to define a variable dimension of a corresponding one of said sockets.

4. The distraction clamp as recited in claim 1 wherein said pin clamp assembly further comprises two pin clamp segments connected to one another to define said bracket.

5. The distraction clamp as recited in claim 4 further comprising at least one pin clamp connector adjustably interconnecting said two pin clamp segments to one another, independent of said clamp connector, to define an adjustable retaining configuration of said bracket for a plurality of pins.

6. The distraction clamp as recited in claim 1 wherein said rod clamp assembly further comprises two connectors each disposed in interconnecting relation between a different one of said two clamps and said clamp connector.

7. The distraction clamp as recited in claim 6 wherein each of said connectors is configured to movably interconnect a corresponding one of said two clamps to said clamp connector.

8. The distraction clamp as recited in claim 7 wherein each of said connectors is configured to rotationally interconnect a corresponding one of said two clamps to said clamp connector in adjustable relation to said bracket.

9. The distraction clamp as recited in claim 8 wherein each of said connectors comprises a third mating surface; each of said retainers comprises a fourth mating surface; correspondingly disposed ones of said third and fourth mating surfaces disposed in adjustable retaining engagement with one another to define a variable orientation of said rod clamp assembly.

\* \* \* \* \*